United States Patent [19]

Traina

[11] Patent Number: 5,077,480

[45] Date of Patent: * Dec. 31, 1991

[54] TRANSMISSOMETER HAVING SOLID STATE LIGHT SOURCE

[76] Inventor: John E. Traina, 303 N. Rose Dr., Glenshaw, Pa. 15116

[*] Notice: The portion of the term of this patent subsequent to Jun. 26, 2007 has been disclaimed.

[21] Appl. No.: 524,845

[22] Filed: May 18, 1990

Related U.S. Application Data

[63] Continuation-in-part of Ser. No. 234,428, Feb. 22, 1988.

[51] Int. Cl.$^5$ ............... G01N 15/06; G01N 21/49; G01N 21/85
[52] U.S. Cl. ..................... 250/575; 356/435
[58] Field of Search ........... 250/575, 574; 356/435, 356/434, 433

[56] References Cited

U.S. PATENT DOCUMENTS

| | | | |
|---|---|---|---|
| 3,562,524 | 2/1971 | Moore | 250/43.5 |
| 3,617,756 | 11/1971 | Sick | 250/218 |
| 3,696,247 | 10/1982 | McIntosh et al. | 250/83.3 |
| 3,860,818 | 6/1975 | Stalder et al. | 250/343 |
| 3,953,127 | 4/1976 | Ahlquist et al. | 250/574 |

OTHER PUBLICATIONS

Title 40, Code of Federal Regulations, Part 60, Appendix B, 1988 edition, pp. 919–946.

Primary Examiner—Davis L. Willis
Assistant Examiner—T. Davenport
Attorney, Agent, or Firm—Ingersoll Buchanan

[57] ABSTRACT

An improved transmissometer of the type which has a visible light source and is responsive to peak and mean spectral responses between 500 nm and 600 nm and optical assembly therefor contains a solid state light source preferably a light emitting diode. The light source emits a low level light beam that is split, part of which is passed through a gaseous sample then directed to a detector while the other part is directed to a second detector. Electronic components are provided to amplify the signal that has passed through the sample providing high gain, low noise amplification and use signals from the detectors to control the light source and determine opacity of the sample.

23 Claims, 2 Drawing Sheets

TRANSMISSOMETER HAVING SOLID STATE LIGHT SOURCE

CROSS REFERENCE TO RELATED APPLICATION

This is a continuation-in-part of my United States patent application Ser. No. *234,282*, filed Feb. 22, 1988, now pending.

FIELD OF INVENTION

This invention generally relates to transmissometers of the type wherein the density, transmission or opacity of a gaseous sample is measured as a function of the attenuation of a light beam passed through the sample. This invention relates to transmissometers which are used for measuring density, transmission or opacity of stacks or ducts which contain the gases resulting from burning fossil fuel.

DESCRIPTION OF THE PRIOR ART

The use of optical devices to measure the density or opacity of gaseous materials, smoke for example, is known in the art. Examples may be seen in U.S. Pat. Nos. 3,600,590; 3,617,756; 3,810,697 and 3,917,957.

Typically one type of transmissometer is comprised of an optical assembly having a light source which emits a light beam. The light beam is split with one portion being directed to a reference detector and the remaining portion being directed through a sample to a retro-reflector. The retro-reflector reflects the light beam back through the sample to a signal detector. The light beam striking the signal detector is compared electronically to the light beam striking the reference detector to determine opacity.

The United States Environmental Protection Agency has established standards for optical devices used to measure pollutants. These standards are set forth in Title 40, Code of Federal Regulations, Part 60, Appendix B Performance Spec. 1. These regulations require the light source to be in the visible spectrum. Specifically, the peak and mean spectral responses must occur between 500 nm and 600 nm. The response at any wavelength below 400 nm or above 700 nm must be less than 10 percent of the peak spectral response. Peak spectral response is the wavelength of maximum sensitivity of the transmissometer. Spectral response is the wavelength that is the arithmetic mean value of the wavelength distribution for the effective spectral response curve of the transmissometer.

The transmissometers of the prior art for stacks and ducts all use a tungsten incandescent light bulb as the light source. Consequently, the light source is relatively large and needs substantial electrical power. Other shortcomings of light bulbs as light sources are that the associated electrical components such as the socket, transformer and wiring are heavier and less rugged as compared to a solid state light source configuration. Also, light bulbs give off heat; light bulbs have a shorter life; light bulbs require spectral filters to meet EPA color requirements; and light bulbs cannot be directly modulated effectively.

Prior to the present invention the art believed that light emitting diodes and other low power light sources could not be used in a transmissometer because the light beam which they produce is too dim to operate over the general application requirement for stacks and ducts ranging from 0.5 feet to 40 feet between the optical assembly and retro reflector.

U.S. Pat. No. 4,249,244 to Shofner et al. discloses an electro-optical system and method for providing automatically-compensating traceable calibration and zoning for light scattering devices. The preferred device uses a laser beam as a substantially monochromatic light source and optics for collection and focusing the beam onto a detector after it passes through a sample. This device is not a transmissometer and uses back scattering as the detection technique. Shofner discloses that a light emitting diode may be substituted for the laser in his device. However, prior to the present invention, the art has not considered it possible to substitute a light emitting diode in transmissometers of the type which meet EPA standards for pollution detection and measurement. The reason for this belief is that there are vast differences in power output between lasers and diodes. A typical laser, such as a pulse diode laser, would be used in Shofner's device and would provide a signal of over a watt per square centimeter. The LED in my device produces no more than ten millowatts in a beam 15 centimeters in diameter which has energy levels below 60 microwatts per square centimeter. Shofner does not teach how an LED light source with such reduced power can be successfully substituted. Prior to the present invention, those skilled in the art believed that such a substitution could not be made in a transmissometer which met EPA standards.

Shofner's device is shown in a high pressure, small diameter pipe (Column 7, lines 16–26). My device can be used in large smoke stacks as large as 42 feet in diameter as well as smoke stacks typically 3 feet or more in diameter. There is no teaching or appreciation in Shofner of the fact that light emitting diodes typically do not produce sufficient energy to traverse substantial distances and provide a useful signal after transversing those distances. Since Shofner is working with small pipes the energy difference between lasers and LED's is less critical. Prior to the present invention nobody had discovered how to use LED's as a light source for large duct opacity monitors. The state of the art prior to the present invention is aptly reflected in my U.S. Pat. No. 3,917,959 which utilizes an incandescent light source. Similarly, in U.S. Pat. No. 4,589,775 to Milhous, the light source of FIG. 2 is illustrated as an incandescent bulb. Significant electro-optical circuitry is required when incandescent light sources are used. If the art knew of a way to use light emitting diodes in transmissometers, they would have avoided the circuitry required for an incandescent light source which would have resulted in substantial savings. Consequently, the compact size and low power requirements of diodes and other advantages are not available in prior art transmissometers.

Consequently, there is a need for a transmissometer which has a solid state light source.

The Environmental Protection Agency has established standards for transmissometers which are set forth in Title 40, Code of Federal Regulations, Part 60, Appendix B Performance Spec. 1. Many users will not buy a transmissometer which does not meet these standards. Consequently, it is advantageous for a transmissometer to meet these standards. Although the standards are quite detailed and extensive, two portions are particularly of interest to my type of device. The light source must produce a visual beam. The detector which detects the beam after the beam passes through the sample must have peak and mean spectral responses between 500 nm and 600 nm.

SUMMARY OF THE INVENTION

My improved transmissometer measures all transmitted energy and contains a solid state light source which requires low power, is lighter and more rugged, gives off low heat, has longer life and can be directly modulated and meets the requirements of 40 CFR 60 Appendix B. Performance Spec. 1. Specifically, my transmissometer has a visible light source and produces peak and mean spectral responses between 500 nm and 600 nm. In this general class of transmissometer, a light beam, modulated at a pre-selected frequency, is passed through a gaseous sample.

In my apparatus the light source is modulated and then split. One portion goes to a reference detector and the second portion passes through the sample. This second portion is reflected back through the sample by a retro-reflector positioned across the sample from the source of the modulated beam. The components of the improved transmissometer include a light emitting diode and associated circuitry which generates a light beam that passes through and is reflected back through a sample.

DESCRIPTION OF THE PREFERRED EMBODIMENTS

Figure 1:
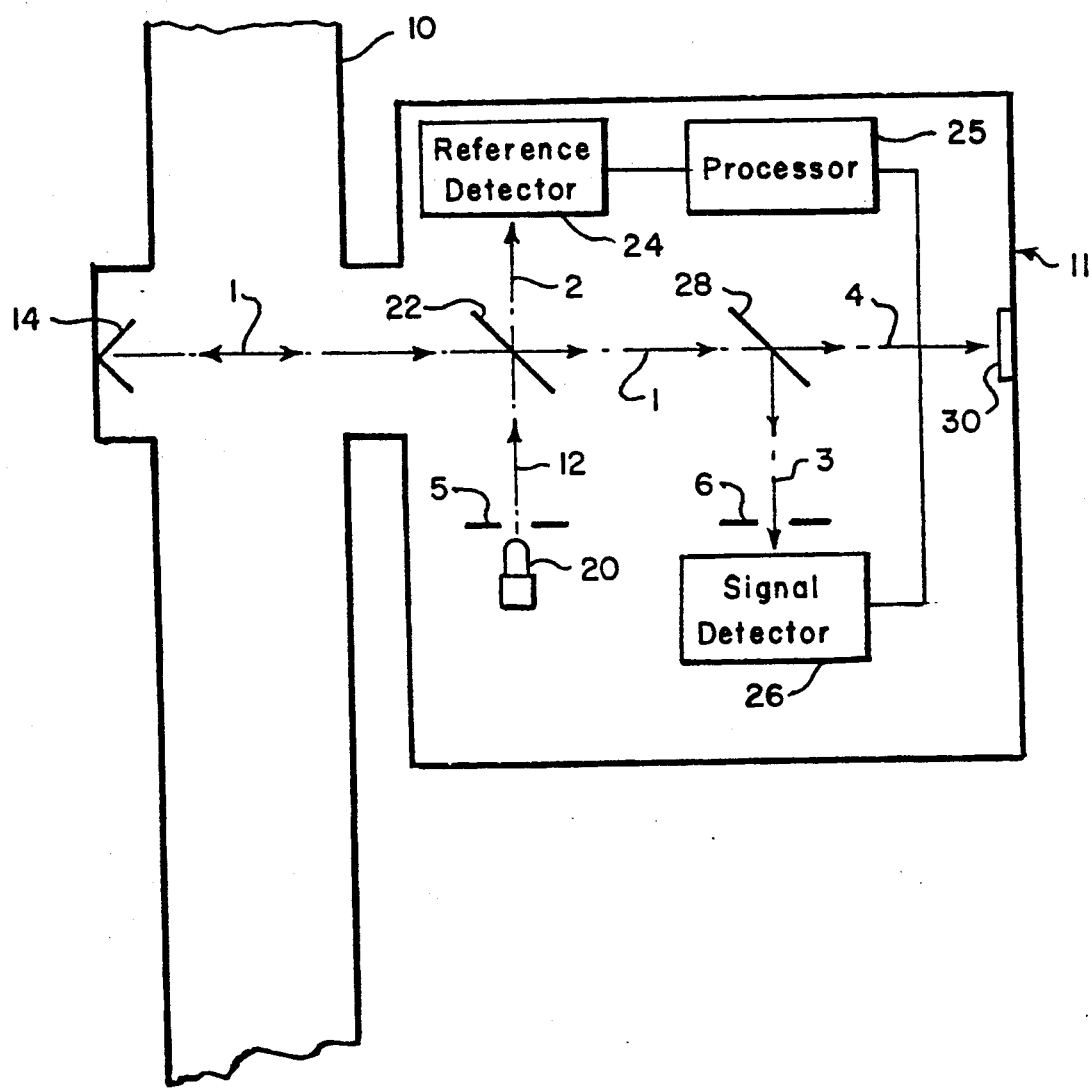
FIG. 1 is a schematic diagram of a transmissometer which may contain my improved optical assembly.

FIG. 1 shows a configuration of a double pass transmissometer connected to a conduit 10 through which a gaseous sample passes. The transmissometer is comprised of an optical assembly 11 which produces a light beam 1 that passes through the gaseous sample in conduit 10 and is reflected by retro-reflector 14 to the optical assembly 11. Within the optical assembly 11 is a light source 20 which produces a visible light beam 12. The light beam 12 travels through the projection aperture 5 to a beam splitter 22 which splits beam 12 into a first light beam 1 and a second light beam 2. The second light beam 2 is directed to a reference detector 24 which translates the light beam 2 into an electrical signal. The first light beam 1 is reflected from retro-reflector 14 to a signal detector 26. If desired, the reflected beam 1 may be split by beam splitter 28 into a third light beam 3 and a fourth light beam 4. The third light beam 3 is directed through field stop 6 to a signal detector 26 and the fourth beam 4 is directed to a window 30. The signal detector 26 coverts the third beam 3 into an electrical signal. A processor 25 or other comparable circuitry receives the electrical signals from detectors 24 and 26 and processes them. Since the signal from reference detector 24 corresponds to a light beam that has not passed through the sample, and the signal from signal detector 26 corresponds to a light beam that has passed through the sample, the two signals can reveal the opacity of the sample. Although I prefer to provide a retro-reflector to reflect the light beam back through the sample, such a double pass arrangement is not necessary to my invention. A single pass configuration can be obtained by placing signal detector 26 in the position of retro-reflector 14.

Within the optical assembly lenses can be used to focus the various light beams. For ease of illustration, I have not shown any such lenses but those skilled in the art will recognize that such lenses could be and commonly are used. I have also not shown chopping means such as that taught in my U.S. Pat. No. 3,917,957. However, it should be understood that chopping means could be used.

Figure 2:
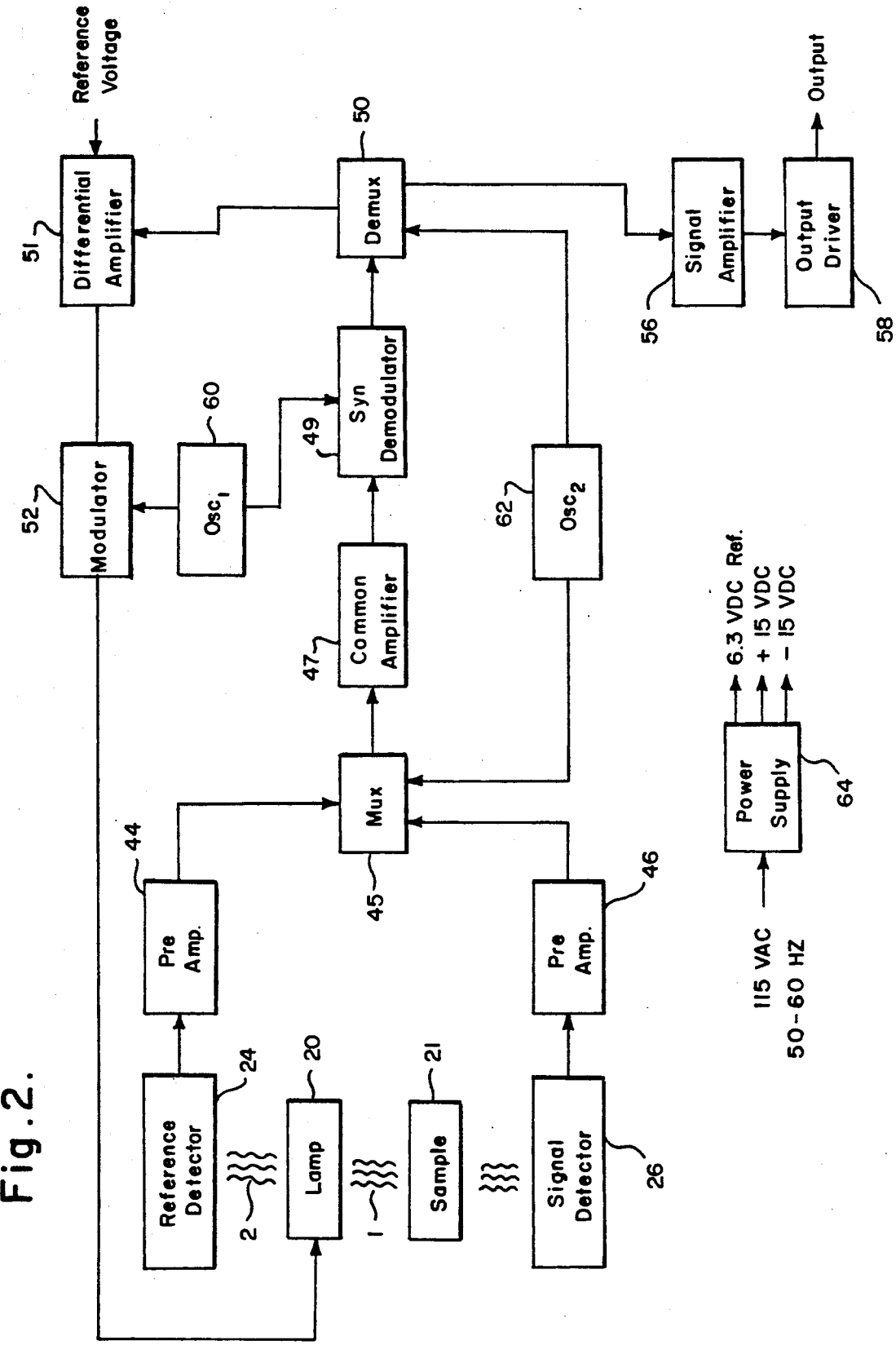
FIG. 2 is a block diagram of my improved optical assembly.

In the transmissometers of the prior art, light source 20 is a tungsten incandescent light bulb. However, I have found that the circuitry and components diagramed in FIG. 2 will permit the use of a light emitting diode. Such diodes presently produce not more than ten milliwatts in a beam 15 centimeters in diameter which has energy levels below 60 microwatts per square centimeter. Consequently, the circuitry must have a low noise to signal ratio in order to detect the beam after it passes through the optical sections. Having discovered how to do this, I can create a compact, lighter, low heat generating light source. Moreover, the entire light source and components of FIG. 2 can be assembled into a solid state circuit which can be more simply powered. The circuitry of FIG. 2 is intended to be used in a transmissometer of the type illustrated in FIG. 1. Most of the components of the circuit of FIG. 2 would be included in the circuitry identified by box 25 of FIG. 1. Where like components appear in both figures, I have used the same reference number.

Referring to FIG. 2, I provide a light source 20 which produces light beams 1 and 2. The first light beam passes through the sample 21 and is reflected to signal detector 26. The second beam is directed to reference detector 24. The detectors 26 and 24 generate electrical signals that correspond to the light beams 1 and 2 which they receive. The signals pass through low noise preamplifiers 44 and 46 to multiplexer 45. The multiplexer 45 alternatively sends the reference signal and the sample signal to a common amplifier 47. The common amplifier 47 sends the amplified signals to a synchronous demodulator 49. The demodulator 49 removes the carrier portion from the signals and supplies the signals alternatively to a demultiplexer 50. The signals are then separated and the reference signal is sent to a differential amplifier 51. In this amplifier the reference signal is compared against a reference voltage of preferably 6.3 volts. The output of the differential amplifier 51 will continually change until the reference signal from the demultiplexer 50 equals a reference voltage. The differential amplifier output feeds a modulator 52. I prefer to provide an oscillator 53 to provide a carrier signal to the modulator 52. In the modulator 52, the off/on signal of the carrier is controlled in amplitude by the signal from the differential amplifier 51. The modulator drives the light source 20 which completes the lamp control loop. The result of this loop is a constant level amplitude modulated light output from the light source.

The sample signal which is generated by sample detector 26 is processed in the same manner as the reference signal until it reaches demultiplexer 50. The demultiplexer 50 sends the sample signal straight to a signal amplifier 56 and output driver 58 for gauges or other indicators (not shown). These devices create a display such as a number or a graph which tells the operator about the opacity of the sample. With the light source output held constant by the reference loop, the signal reaching the signal amplifier will only change if the sample path changes its attenuation.

The adjustments in the signal amplifier and output drive are used to typically set the output to 20 ma with no attenuation (0% opacity) and 4 ma with the light blocked off completely (100% opacity).

There are two oscillators 60 and 62 in the unit. One provides the carrier signal at 2.5 KHZ, the other provides the multiplex/demultiplex control signals.

The power supply 64 provides three regulated DC voltages as shown. The 6.3 volts is the reference voltage and is temperature compensated.

I have found that the following components can be used in my circuit:

| Reference No. | Description | Part No. | Supplier |
|---|---|---|---|
| 20 | LED | ESPY-5701 | A. C. Interface |
| 24 and 26 | Detectors | PIN 5DP | United Detector |
| 44 and 46 | Pre-amp | LF 257H | National Sem. |
| 45 | Multiplexer | IT400 A | Intersil |
| 47 | Amplifier | LF257H | National Sem. |
| 49 | Demodulator | 3510A M | Burr-Brown |
| 50 | Demultiplexer | IH401AE | Intersil |
| 57 | Differential Amp. | TLO84CN | Texas Instruments |
| 52 | Modulator | IT400A | Intersil |
| 56 | Amplifier | TLO84CN | Texas Instruments |
| 60 | Oscillator | CD4047BE | RCA |
| 62 | Oscillator | TLO84CN | Texas Instruments |

I have also found that coating the optical elements with an AR coating also improves the performance of my device.

When the above listed components have been used in a transmissometer made in accordance with this invention, they have produced a visible green light. The peak and mean spectral responses have been between 500 and 600 nm and less than 10% of each peak response is outside the desired 400 to 700 nm region comprising the visible light spectra. Also, the light source angle of projection and photodetector angle of view are less than 3 degrees from optical axis. Thus, the device is within EPA requirements that those angles not exceed 5 degrees.

When fully assembled my optical assembly, and the transmissometer which contains this assembly, are rugged, precision, electro-optic instruments. The stack equipment can operate within a temperature range of −40 to +150 degrees Fahrenheit. The transmissometer will meet or exceed the current standards reported in Title 40 of the Code of Federal Regulations at Part 60, Appendix B Performance Spec. 1.

While I have shown and described certain present preferred embodiments of my invention, it should be distinctly understood that the invention is not limited thereto, but may be variously embodied within the scope of the following claims.

I claim:

1. An improved transmissometer of the type which measures light energy having a light source which produces a visible beam and a detection means which light source emits a light beam that passes through a sample to the detection means, the detection means produces an electrical signal responsive to the light beam and the transmissometer has peak and mean spectral responses between 500 nm and 600 nm wherein the improvement comprises a solid state light source of known intensity and amplification means connected to the detection means for amplifying the electrical signal produced by the light source said amplification means providing high gain, low noise amplification.

2. The improved transmissometer of claim 1 wherein the solid state light source is a light emitting diode.

3. An improved optical assembly which produces a light beam for a transmissometer of the type wherein the light beam is passed through a gaseous sample, the assembly comprised of:

a) a solid state light source which emits a visible light beam;

b) a reference detector which converts a light beam to an electrical signal;

c) a signal detector which converts a light beam to an electrical signal and has peak and mean spectral responses between 500 nm and 600 nm;

d) a beam splitter sized and positioned to split the light beam into a first beam and a second beam, to direct the first beam to the reference detector, and to direct the second beam through the sample to the signal detector;

e) a preamplifier connected to the reference detector and a second preamplifier connected to the signal detector to receive an electrical signal therefrom which amplifies the electrical signal;

f) a multiplexer connected to the preamplifiers which alternatively send a signal received through the preamplifier from the reference detector and a signal received through the second preamplifier from the signal detector;

g) an amplifier connected to receive signals from the multiplexer;

h) a demodulator connected to receive signals from the amplifier and remove a carrier portion from the signals;

i) a demultiplexer connected to receive signals from the demodulator and which separates the signals;

j) a differential amplifier connected to receive signals from the demultiplexer and which compares the received reference signal to a reference voltage and produces an output signal which will continually change until a reference signal is received from the demultiplexer which equals the reference voltage;

k) a modulator connected to receive a signal from the differential amplifier and having an output which is connected to the light source in a manner so that the output from the modulator determines intensity of the light beam emitted by the light source;

l) a signal amplifier connected to the demultiplexer for receiving a signal from the demultiplexer corresponding to the opacity of the sample; and m) output means connected to receive a signal from the signal amplifier and creates a display corresponding to the signal in a manner selected by an operator to tell the operator the opacity of the sample.

4. The improved optical assembly of claim 3 also comprising a window and a second beam splitter positioned to receive the second beam from the sample and split the second beam into a third beam which is directed to the signal detector and a fourth beam which is directed to the window.

5. The improved optical assembly of claim 4 wherein the second beam splitter is an 80/20 beam splitter.

6. The improved optical assembly of claim 3 wherein the beam splitter is a 50/50 beam splitter.

7. The improved optical assembly of claim 3 wherein the light source is a light emitting diode.

8. The improved assembly of claim 3 also comprising an oscillator connected to the modulator and demodulator.

9. The improved assembly of claim 3 also comprising a second oscillator connected to the multiplexer and the demultiplexer.

10. The improved assembly of claim 3 also comprising a retro-reflector positioned to reflect the second beam back through the sample to the signal detector.

11. The improved assembly of claim 3 wherein an AR coating is applied to at least one optical element.

12. The improved transmissometer of claim 1 also comprising means for maintaining the light source at constant intensity.

13. The improved transmissometer of claim 1 wherein the light source is a broad spectrum light source.

14. The improved transmissometer of claim 1 wherein the transmissometer is suitable for measuring light attenuation in stacks and ducts which contain light obscuring materials resulting from burning fossil fuel.

15. An improved transmissometer of the type wherein a visible light beam is produced by an optical assembly passed through a gaseous sample, to at least one detector wherein the improvement comprises:
  a) a solid state light source which emits a visible light beam;
  b) a reference detector which converts a light beam to an electrical signal;
  c) a signal detector which converts a light beam to an electrical signal and has peak and mean spectral responses between 500 nm and 600 nm;
  d) a beam splitter sized and positioned to split the light beam into a first beam and a second beam, to direct the first beam to reference detector, and to direct the second beam through the sample to the signal detector;
  e) a preamplifier connected to the reference detector and a second preamplifier connected to the signal detector to receive an electrical signal therefrom which amplifies the electrical signal;
  f) a multiplexer connected to the preamplifier which alternatively sends a signal received through the preamplifier from the reference detector and a signal received through the second preamplifier from the signal detector;
  g) an amplifier connected to receive signals from the multiplexer;
  h) a demodulator connected to receive signals from the amplifier and remove a carrier portion from the signals;
  i) a demultiplexer connected to receive signals from the demodulator and which separates the signals;
  j) a differential amplifier connected to receive the reference signal from the demultiplexer and which compares the received signal to a reference voltage and produces an output signal which will continually change until a signal is received from the demultiplexer which equals the reference voltage;
  k) a modulator connected to receive a signal from the differential amplifier and having an output which is connected to the light source in a manner so that the output from the modulator determines intensity of the light beam emitted by the light source;
  l) a signal amplifier connected to the demultiplexer for receiving a signal from the demultiplexer corresponding to the opacity of the sample; and
  m) output means connected to receive a signal from the signal amplifier and creates a display corresponding to the signal in a manner selected by an operator to tell the operator the opacity of the sample.

16. The improved transmissometer of claim 15 also comprising a window and a second beam splitter positioned to receive the second beam and split the second beam into a third beam which is directed to the signal detector and a fourth beam is directed to the window.

17. The improved transmissometer of claim 16 wherein the second beam splitter is an 80/20 beam splitter.

18. The improved transmissometer of claim 15 wherein the beam splitter is a 50/50 beam splitter.

19. The improved transmissometer of claim 15 wherein the light source is a light emitting diode.

20. The improved transmissometer of claim 15 also comprising an oscillator connected to the modulator and demodulator.

21. The improved transmissometer of claim 15 also comprising a second oscillator connected to the multiplexer and the demultiplexer.

22. The improved transmissometer of claim 15 also comprising a retro-reflector positioned to reflect the second beam back through the sample to the signal detector.

23. The improved transmissometer of claim 15 wherein an AR coating is applied to at least one optical element.

* * * * *

UNITED STATES PATENT AND TRADEMARK OFFICE
CERTIFICATE OF CORRECTION

PATENT NO. : 5,077,480 B1 Page 1 of 1
APPLICATION NO. : 07/524845
DATED : July 2, 1996
INVENTOR(S) : John E. Traina It is certified that error appears in the above-identified patent and that said Letters Patent is hereby corrected as shown below:

Column 2, claim 1, line 1, change "mean" to – –means– –.

Signed and Sealed this

Twenty-ninth Day of August, 2006

JON W. DUDAS
*Director of the United States Patent and Trademark Office*

REEXAMINATION CERTIFICATE (2945th)
United States Patent [19]
Traina

[11] B1 5,077,480
[45] Certificate Issued Jul. 2, 1996

[54] TRANSMISSOMETER HAVING SOLID STATE LIGHT SOURCE

[75] Inventor: John E. Traina, Glenshaw, Pa.

[73] Assignee: United Sciences, Inc., Gibsonia, Pa.

Reexamination Request:
No. 90/003,864, Jun. 16, 1995

Reexamination Certificate for:
Patent No.: 5,077,480
Issued: Dec. 31, 1991
Appl. No.: 524,845
Filed: May 18, 1990

[51] Int. Cl.$^6$ .................. G01N 15/06; G01N 21/49; G01N 21/85
[52] U.S. Cl. .......................... 250/575; 356/435
[58] Field of Search .................. 250/573, 574, 250/575, 576, 205, 226; 356/432, 433, 434, 435, 436, 437, 438, 439

[56] References Cited

U.S. PATENT DOCUMENTS

| | | | |
|---|---|---|---|
| 3,857,641 | 12/1974 | Gass | 356/207 |
| 3,917,957 | 11/1975 | Ansevin et al. | 250/573 |
| 3,953,127 | 4/1976 | Ahlquist | 356/103 |
| 4,249,244 | 2/1981 | Shofner et al. | 250/573 |
| 4,589,775 | 5/1986 | Milhous, Jr. et al. | 356/439 |

OTHER PUBLICATIONS

German Federal Environmental Agency, Air Quality Maintenance Manual for Continuous Monitoring of Emissions, Reports Feb. 1984, translation of Berichte Feb. 1984, pp. 75–76.

Data Sheet 20-20.10 EN of Hermann & Braun AG, Oct., 1989, Intrans D Visible Emission Monitor.

Codel Operating Instructions, Apr. 1987.

RM 41 StaubgehaltmeBgerat German Version of RM 41 Smoke/Dust Density Monitor listed on p. 2, 1975.

Brochure of Codel, 101 Opacity Monitor–For Reliable, Low Opacity Monitoring, Feb., 1987.

Brochure of Codel, 200 Opacity Monitor–for the Ultimate in Opacity Monitoring.

RM 41 Smoke/Dust Density Monitor, Dec. 6, 1981.

Brochure of Codel, 101 Opacity Monitor–For Reliable, Low Opacity Monitoring, Feb. 1987.

Brochure of Codel, 200 Opacity Monitor–for the Ultimate in Opacity Monitoring.

*Primary Examiner*—Edward P. Westin

[57] ABSTRACT

An improved transmissometer of the type which has a visible light source and is responsive to peak and mean spectral responses between 500 nm and 600 nm and optical assembly therefor contains a solid state light source preferably a light emitting diode. The light source emits a low level light beam that is split, part of which is passed through a gaseous sample then directed to a detector while the other part is directed to a second detector. Electronic components are provided to amplify the signal that has passed through the sample providing high gain, low noise amplification and use signals from the detectors to control the light source and determine opacity of the sample.

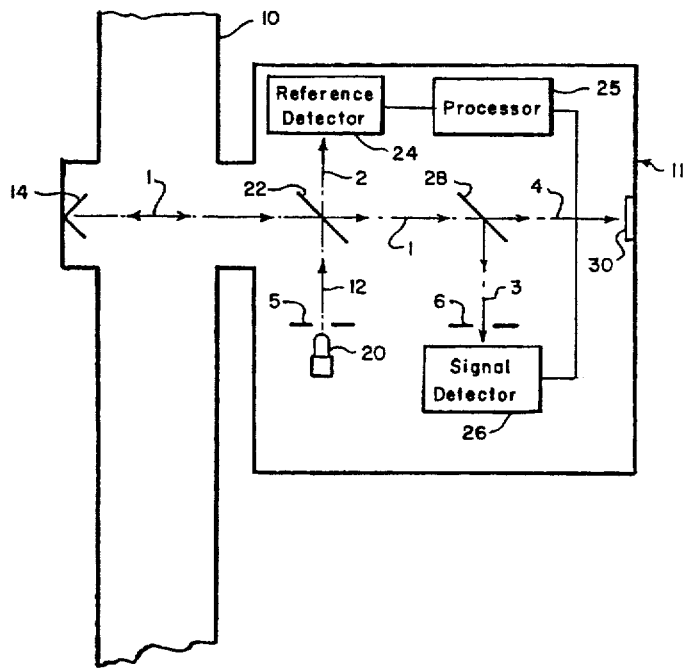

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 3–11 and 15–23 is confirmed.

Claim 1 is determined to be patentable as amended.

Claims 2 and 12–14, dependent on an amended claim, are determined to be patentable.

New claims 24, 25 and 26 are added and determined to be patentable.

1. An improved transmissometer of the type which measures light energy having a light source which produces a visible beam and a detection means which light source emits a light beam that passes through a sample to the detection means, the detection means produces an electrical signal responsive to the light beam and the transmissometer has peak and mean spectral responses between 500 nm and 600 nm wherein the improvement comprises a solid state light source of known intensity and amplification means connected to the detection mean for amplifying the electrical signal produced [by] *in response to the light beam from* the light source said amplification means providing high gain, low noise amplification *to produce an amplified signal having adequate signal to noise ratio sufficient to indicate opacity of a fluid passing through a stack or duct in excess of 3 feet in diameter but not greater than 42 feet in diameter.*

*24. The improved transmissometer of claim 1 also comprising a synchronous demodulator connected to the detecting means.*

*25. An improved transmissometer of the type which measures light energy having a light source which produces a visible beam and a detector which light source emits a light beam that passes through a sample to the detector which produces an electrical signal responsive to the light beam and the transmissometer has peak and mean spectral responses between 500 nm and 600 nm wherein the improvement comprises a solid state light source of known intensity, and an amplifier connected to the detector for amplifying the electrical signal produced in response to the light beam from the light source said amplifier providing high gain, low noise amplification to produce an amplified signal having adequate signal to noise ratio sufficient to indicate opacity of a fluid passing through a stack or duct which has a diameter in excess of 3 feet but not greater than 42 feet.*

*26. The improved transmissometer of claim 25 also comprising a synchronous demodulator connected to the detector.*

\* \* \* \* \*